(12) United States Patent
Delogé et al.

(10) Patent No.: US 6,673,076 B2
(45) Date of Patent: Jan. 6, 2004

(54) TARGETING APPARATUS FOR USE IN RESECTIONING A FEMUR WHEN PERFORMING TRANSFEMORAL OSTEOTOMY

(75) Inventors: Nicolas Delogé, Douvres (FR); Jean-Pierre Brée, Fontaine Etoupefour (FR); Arnaud Aux Epaules, Saint-aubin-sur-mer (FR); Philippe Lavieille, Caen (FR); Christophe Cueille, Missy (FR)

(73) Assignee: Benoist Girard SAS (FR)

( * ) Notice: Subject to any disclaimer, the term of this patent is extended or adjusted under 35 U.S.C. 154(b) by 67 days.

(21) Appl. No.: 10/008,116

(22) Filed: Nov. 8, 2001

(65) Prior Publication Data
US 2002/0116003 A1 Aug. 22, 2002

(30) Foreign Application Priority Data

Nov. 13, 2000 (GB) ................................. 0027698
Nov. 13, 2000 (GB) ................................. 0027700
Mar. 8, 2001 (GB) ................................. 0105779

(51) Int. Cl.$^7$ ................................. A61B 17/58
(52) U.S. Cl. ................................. 606/87; 606/88
(58) Field of Search ................. 606/87, 89, 96, 606/98, 86, 64, 62, 60, 53

(56) References Cited

U.S. PATENT DOCUMENTS

| | | | | |
|---|---|---|---|---|
| 2,362,957 A | * | 11/1944 | Hackett | 606/86 |
| 3,945,377 A | * | 3/1976 | Kronner | 606/96 |
| 4,037,592 A | | 7/1977 | Kronner | |
| 4,187,840 A | * | 2/1980 | Watanabe | 606/86 |
| 4,541,424 A | | 9/1985 | Grosse et al. | |
| 4,865,025 A | * | 9/1989 | Buzzi et al. | 606/96 |
| 4,883,048 A | * | 11/1989 | Purnell et al. | 606/96 |
| 5,078,719 A | | 1/1992 | Schreiber | |
| 5,176,681 A | | 1/1993 | Lawes et al. | |
| 5,207,682 A | * | 5/1993 | Cripe | 606/96 |
| 5,306,278 A | | 4/1994 | Dahl et al. | |
| 5,334,192 A | | 8/1994 | Behrens | |
| 5,374,271 A | * | 12/1994 | Hwang | 606/86 |
| 5,403,322 A | | 4/1995 | Herzenberg et al. | |
| 5,620,449 A | * | 4/1997 | Faccioli et al. | 606/98 |
| 5,665,086 A | | 9/1997 | Itoman et al. | |
| 6,027,506 A | | 2/2000 | Faccioli et al. | |
| 6,102,953 A | | 8/2000 | Huebner | |
| 6,168,628 B1 | | 1/2001 | Huebner | |
| 6,494,913 B1 | | 12/2002 | Huebner | |

FOREIGN PATENT DOCUMENTS

| | | |
|---|---|---|
| DE | 296 12 306 U1 | 2/1997 |
| EP | 0 514 662 A1 | 4/1992 |
| FR | 2 647 006 | 5/1989 |
| FR | 2 686 788 | 8/1993 |
| FR | 2 692 472 | 12/1993 |
| JP | 09075366 A1 | 3/1997 |
| WO | WO-92/01422 | 2/1992 |

* cited by examiner

Primary Examiner—Pedro Philogene
(74) Attorney, Agent, or Firm—Lerner, David, Littenberg, Krumholz & Mentlik, LLP

(57) ABSTRACT

A targeting apparatus for use in resectioning a femur when performing transfemoral osteotomy surgery has a drill guide element which includes a line of drill openings each of which is adapted to guide a drill for drilling holes in the femur. A connector is provided for securing the drill guide element to a femur to be resectioned with the line of openings extending in a proximal/distal direction along the femur.

42 Claims, 8 Drawing Sheets

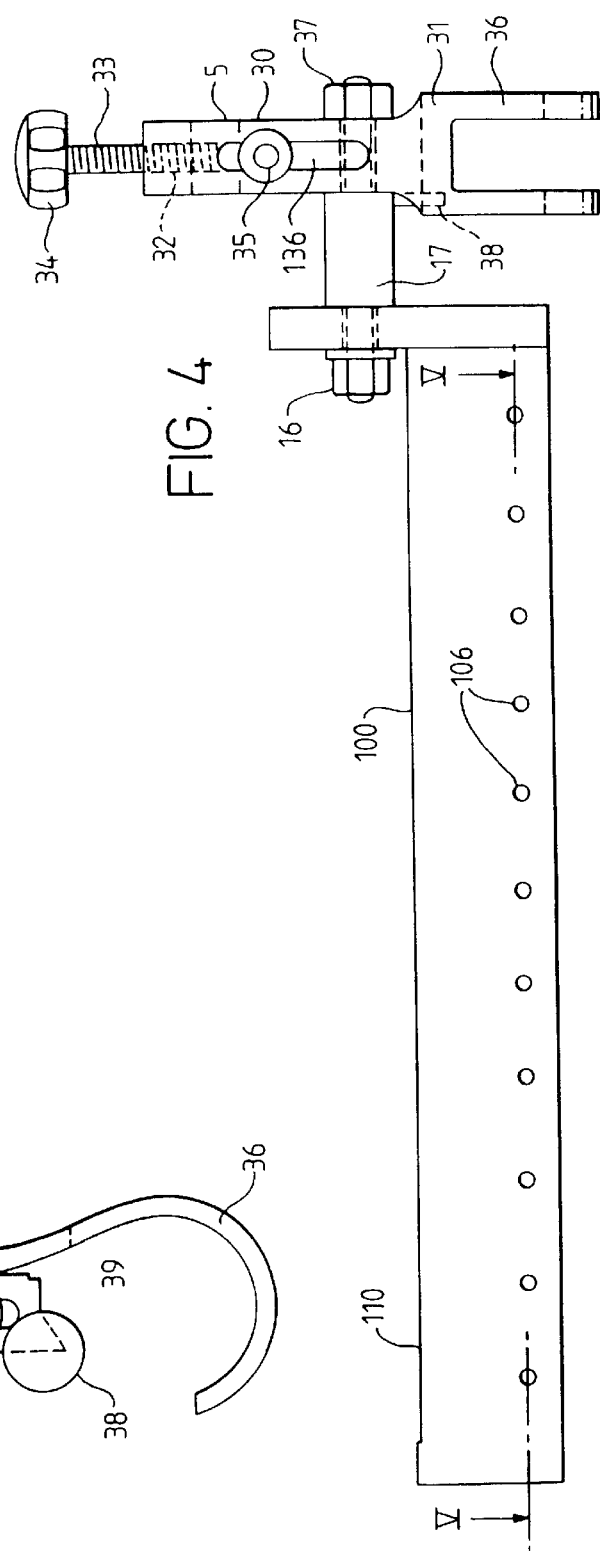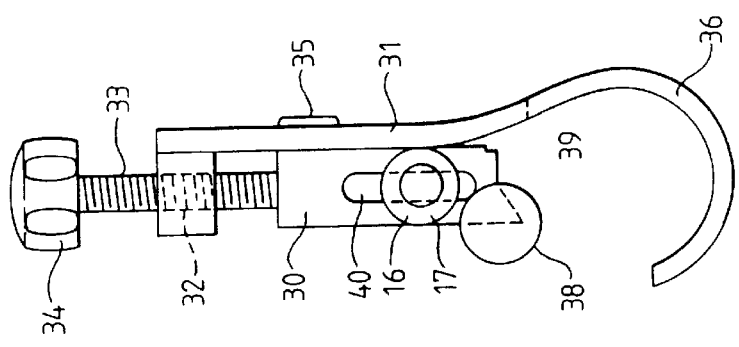

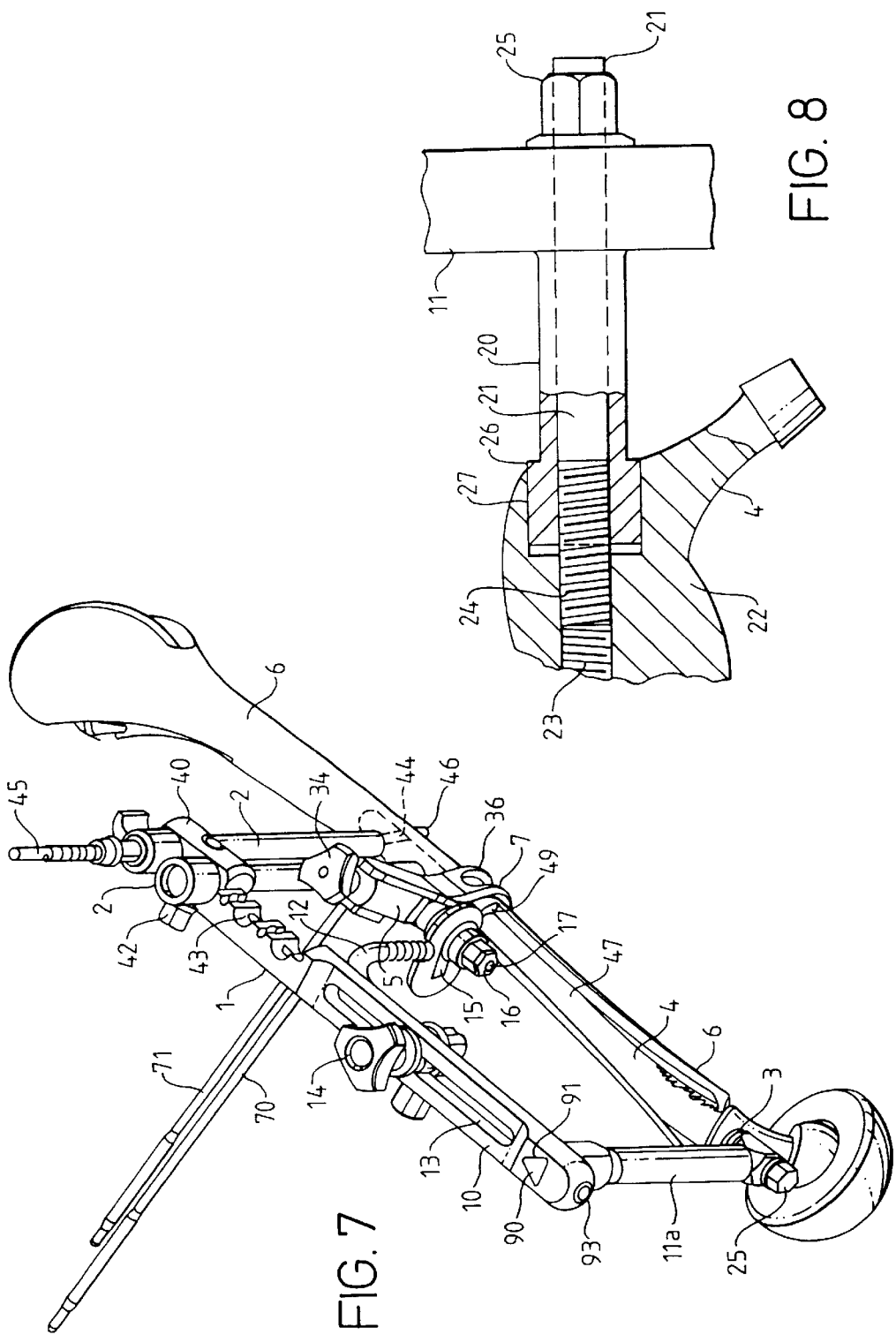

TARGETING APPARATUS FOR USE IN RESECTIONING A FEMUR WHEN PERFORMING TRANSFEMORAL OSTEOTOMY

BACKGROUND OF THE INVENTION

This invention relates to targeting apparatus for use in resectioning a femur when performing transfemoral osteotomy. In this surgical technique the femur is exposed along a proximal/distal line, the soft tissue (skin, muscle) being folded back on each side to expose the bone. The proximal end of the femur is now open as a "window" and a femoral prosthesis is inserted into the bone canal.

The technique requires careful pre-operative planning, usually from X-rays, and it is possible to calculate in advance how far to cut the "window" so that the distal edge of the "window" end can become a datum base.

There are difficulties and disadvantages when using this technique due to the possibilities of damaging the soft tissue when resectioning the bone. The soft tissue has to be opened along a proximal/distal line and the bone then cut along the same line. This is usually done with a saw but it will be appreciated that the cutting of the soft tissues above the saw cut necessary destroys the tissues in the area. When the further two cuts along a proximal/distal line are made in order to allow the two pieces of cut bone to be opened out form the "window" there is again severe damage to the soft tissue and this can severely effect the healing process when the window is subsequently closed.

The present invention is intended to provide instrumentation which can be employed with a technique which will not only avoid damage to the soft tissue but enable the "window" to be more easily closed.

The apparatus according to the invention can also be used with apparatus for performing the remainder of the transfemoral osteotomy.

There are obvious difficulties in assessing the particular angular position of the prosthesis in the femoral canal and the exact location of the resectioning of the femur must be accurately judged. A further difficulty arises with regard to the placement of one or more retaining bolts towards the distal end of the stem of the prosthesis. These bolts, screws or pins pass through the bone, the stem of the prosthesis and out through the other side of the bone thus anchoring the prosthesis in position. It is difficult for surgeons to judge the exact position to drill the holes in the bone to coincide with the holes in the implant and it is also necessary to select the correct angular position for the prosthesis and therefore the holes. It is also difficult to judge the exact distance down the femur for the holes to achieve the correct leg length of the correction.

This apparatus for use in performing transfemoral osteotomy is intended to overcome some of the difficulties referred to above and the present apparatus can be used in conjunction with it.

SUMMARY OF THE INVENTION

According to the present invention a targeting apparatus for use in resectioning a femur when performing transfemoral osteotomy surgery comprises a drill guide element which includes a line of drill opening each of which is adapted to guide a drill and a connector or clamp for rigidly securing the drill guide element to a femur to be resectioned with the line of openings extending in a proximal/distal direction.

The apparatus can be used by securing the drill guide element to the femur and drilling through the line of openings to provide an interrupted cut along the bone. Because the drill passes through the soft tissue it is not completely cut but merely has a series of perforations along its length. Prior to drilling the line of holes in the bone the first proximal/distal saw cut will have been made along the top and the longitudinally extending portion of bone can now be broken away along the line of drill holes. The soft tissue is however still in existence between the remainder of the femur and the separated portion so that it can hold the folded back separated portion in place alongside the remainder of the femur and it also provides anchorage when the window is closed. The same technique is used on the other side of the femur so that a completely open window exposing the femoral canal is produced.

It will be appreciated that the first cut to be made is the transverse cut which provides an exposed end from which the "window" extends in a proximal direction.

Preferably an adjuster is included for altering the angular position of the drill guide element on the femur about a proximal distal axis after it has been secured thereto thus enabling accurate placement of the holes. In order that both sides of the opening can be drilled without readjustment of the apparatus the drill guide element can include two parallel lines of drill openings.

Adjacent drill openings can be angled in relation to each other so that the openings are more clearly spaced apart on the outer side of the element than on the inner side adjacent the femur and preferably each of the entry points of the openings on the outer side of the element serves two or more openings so that there are more entry points for openings on the inner side of the element than on the outer side. This enables a row of closely spaced openings to be drilled on each side.

The drill guide element can also include a guide for guiding a device for exposing the femur along a proximal distal line. This can be in the form of a guide slot through which the surgeon can open the soft tissue and subsequently saw the first longitudinally extending cut in the bone after it has previously been cut transversely.

The drill guide element may conveniently be removably connected to the connector which secures the drill guide to the femur to assist in sterilization and so that the connector can be used in other apparatus.

Preferably the connector for securing the element to the femur is in the form of an adjustable open jawed clamp adapted to partially surround the femur with which it is to be used.

A locator can also be included for locating the connector on a partially resectioned transverse end of the femur after the first transverse cut has been made.

Because of the particular design of the connector or clamp it can also be used in other apparatus for use in performing transfemoral osteotomy.

If the drill guide element is removed from the means for securing it to the femur the securing element can be attached to apparatus as set out in the applicant's co-pending U.S. applications, Ser. Nos. 10/008,336 and 10/011,047 filed on the same day of the present application, claiming priority of British Patent Application Nos. GB-A-00 27698.0 and GB-A-01 05779.3.

The present invention therefore also includes targeting apparatus for use in performing transfemoral osteotomy surgery as set forth above which also includes a support element provided with a drill guide, a connector or clamp for securing the support element to a resectioned femur, a connector for connecting the drill guide element to the support element, and an adjuster for adjusting the angular position of the drill guide in relation to the resectioned femur about a proximal/distal axis in relation to the resectioned femur about a proximal/distal direction.

With this arrangement the connector acts to secure a support element provided with a drill guide to a prosthesis to be implanted and to a resectioned femur, and an adjuster for adjusting the angular position of the drill guide in relation to the resectioned femur about a proximal distal axis.

Thus, this apparatus which incorporates the connector or clamp set forth above can be used to accurately locate the angular position of the drill guide on the prosthesis (anteversion setting) which can be used to drill the holes to take the retaining bolt or bolts in the bone. Preferably the support element includes a connector for connection to the proximal end of the femoral prosthesis and an indicator can be provided to indicate the angular position of the drill guide relative to the resectioned femur.

Thus, after careful X-ray examination, the precise anteversion setting can be decided and this can then be transferred to the apparatus thus ensuring the correct angular position.

This apparatus can also include an adjuster for adjusting the support element to accommodate alternative leg lengths. In order to do this a device can be included to vary the proximal/distal position of the support element in relation to the prosthesis securing means.

The support element is preferably in the form of an L-shaped frame one arm of which carries the drill guide and the femur securing connector and the other arm carrying the connector for connection to the femoral prosthesis which is to be implanted.

With this arrangement the femur clamp or connector which has already been used in opening the "window" can be connected to the L-shaped frame by a bracket which should be adjusted in proximal/distal directions on the frame and in relation to which the connector or clamp can be angularly adjusted about a proximal/distal axis.

BRIEF DESCRIPTION OF THE DRAWINGS

The present invention can be performed in various ways but one embodiment will now be described by way of example and with reference to the accompanying drawings in which:

FIG. 3 is an end elevation of the connector for securing a drill guide element to a femur according to the present invention;

FIG. 4 is a side elevation of the device shown in FIG. 3 attached to the drill guide element of the present invention;

FIG. 7 is a diagrammatic isometric view of apparatus for performing transfemoral osteotomy and incorporating the supporting device shown in FIGS. 3 and 4;

FIG. 8 is a part cross-sectional view of the connector for securing the support element of the apparatus shown in FIG. 7 to a prosthesis to be implanted;

DETAILED DESCRIPTION OF THE PREFERRED EMBODIMENTS

Figure 1:
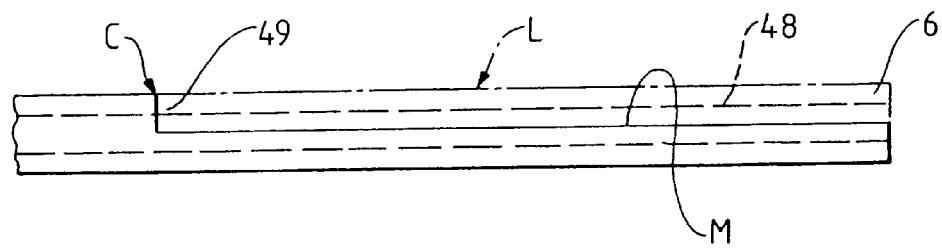
FIG. 1 is a diagrammatic side view of a femur showing how it is cut for performing transfemoral osteotomy surgery.
Figure 2:
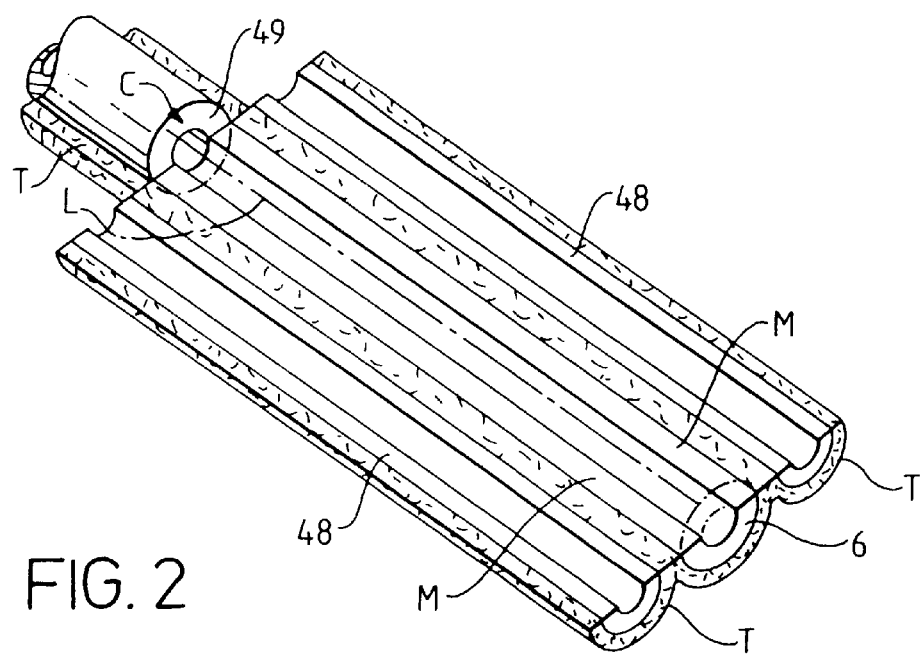
FIG. 2 is a diagrammatic perspective view showing how the "window" is formed in the femur for transfemoral osteotomy surgery.

FIGS. 1 and 2 show, in simplified form, how transfemoral osteotomy surgery is performed. The soft tissue indicated by reference letter T in FIG. 2 is exposed along a proximal/distal line indicated by chain line L in FIG. 2. The soft tissue T is folded back on each side to expose the femur 6 and the bone is resected with three cuts along the same line L with side cuts M and with a transverse cut C. The proximal end of the femur is now opened, as shown in FIG. 2, as a "window". From FIG. 2 it will be seen that an upper quarter 48 is now laid on each side of the remaining part of the bone to expose the bone canal into which the prosthesis is to be inserted.

The preferred embodiment of the present invention relates to apparatus for use in performing this part of the operation and comprises a connector or clamp 5 for securing a drill guide element 100 to a femur 6. This device has a main body portion 30 on which is located a movable clamping jaw 31. The upper part of clamping jaw 31 has a screw threaded bore 32 which has a threaded member 33 one end of which carries an operating handle 34 and the other end of which is rotatably housed in the body 30. Thus, rotation of the handle 34 raises and lowers clamp 31 which is also located by a retaining screw 35 which passes through a slot 136.

The lower end of the open jawed clamp is formed as a pair or curved tines 36 which are adapted to extend around the resectioned femur to which the device is to be clamped.

A guide in the form of disc 38 mounted on body 30 are provided, the disc projecting below the lower end 39 of body 30.

A boss 17 is located in a slot 40 in body 30 and is held by a nut 37 so that the position of the drill guide element 100 can be adjusted to alter the radial distance from femur 6.

The drill guide element 100 comprises a semi-circular support 101 connected to a location bracket 102. This bracket 102 has a slot 103 through which the end of boss 17 can extend, the bracket being held in position by the nut 16.

The surface of bracket 102 is marked with graduations 104 to indicate the relative angular position between the two parts.

The drill guide element 100 includes a line of drill openings 106 along each side and which are adapted to guide a drill, the line of openings extending in a proximal/distal direction. Two parallel lines of drill openings are provided.

Figure 5:
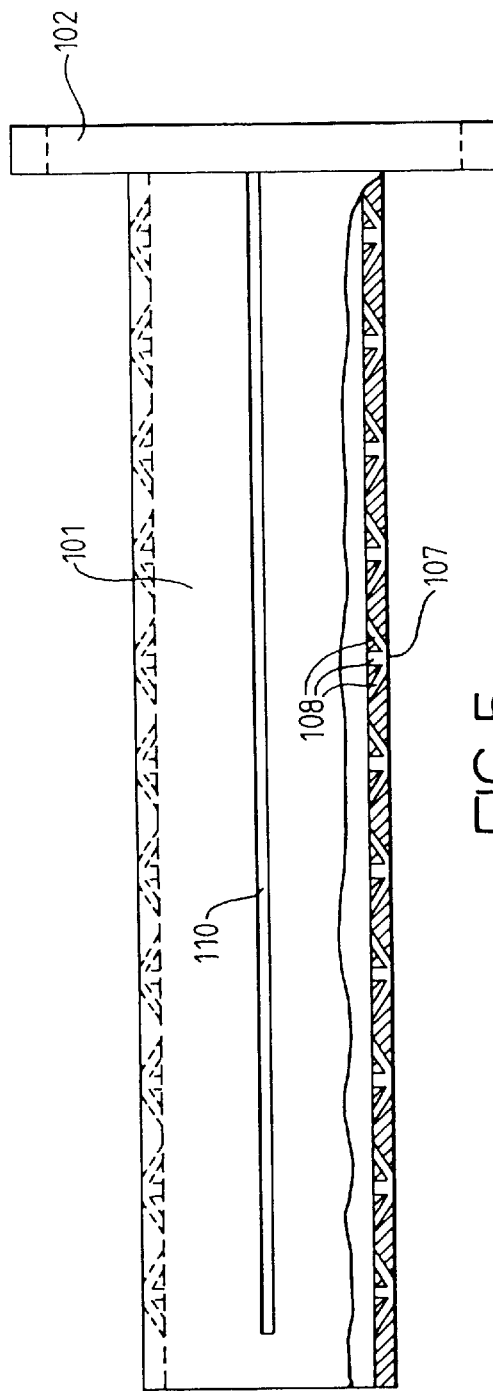
FIG. 5 is a plan view from above of the drill guide element shown in FIG. 4 in part cross-section on the line V—V of FIG. 4.
Figure 6:
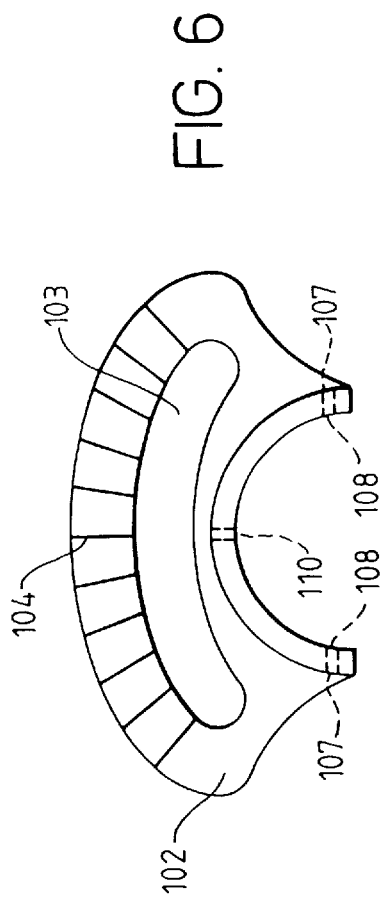
FIG. 6 is an end view of the drill guide element shown in FIG. 5.

Adjacent drill openings 106 are angled in relation to each other and as will be seen from FIG. 5 each of the entry points 107 on the outer side of the element serves three openings on the inner side of the element so that there are more entry points or openings on the inner side of the element than there are on the outer side. This enables a row of closely spaced openings to be drilled on each side.

A guide for guiding an instrument for exposing the femur along a proximal/distal lines are also provided in the form of a guide slot 110 through which the surgeon can open soft tissue and subsequently saw the first longitudinally extending cut in bone 6 after it has been previously transversely cut.

The apparatus according to the present invention is used for resectioning a femur when performing transfemoral osteotomy in the following manner. The surgeon first makes a transverse cut C to expose a proximal end of the femur which can be used as a reference point. This reference point end is exposed by the surgeon and the connector for rigidly securing the drill guide element to the femur, that is the clamp 5, is placed in position by sliding the tines 36 around the bone ensuring that the guide disc 38 is close up against the severed end indicated by reference numeral 49. As mentioned above, the positioning is achieved with a rotative movement. Once in place the handle 34 is operated to close the clamp and maintain it in place. The drill guide element 100 is now placed and locked in position by nut 16. The element extends over the femur and the surgeon now opens the upper part of the femur by severing the soft tissue through the slot 110. This exposes the femur beneath it so that the surgeon can cut a proximal/laterally extending slot. The surgeon now drills a series of holes using the drill guide through the soft tissue and into the bone. The row of holes in the bone provides a row of perforations which can be easily broken away to provide the side cuts M but leaving the two broken away parts of the bone still attached to the remainder by the soft tissue in the manner shown in FIG. 2. The "window" now obtained can be used for the remainder of the operation and leaves the femur ready to receive the prosthesis.

Prior to opening the bone drill guide element 100 will, of course, have been removed by releasing nut 16 but the connector in the form of clamp 5 can be left in position. The same clamp is now used during the remainder of the operation to act as the connector for securing a support element, provided with a drill guide to a prosthesis to be implanted in to a resectioned femur, and securing an adjuster for adjusting the angular position of the drill guide in relation to the resectioned femur about a proximal/distal axis.

This apparatus is shown in FIGS. 7 and 8 comprises a support element 1 in the form of an L-shaped frame having a first arm 10 and a second arm 11. First arm 10 carries drill guides 2 and the femur connector or clamp 5 and the second arm 11 carries the connector 3 for connecting the proximal end of the femoral prosthesis 4.

The femur clamp 5, as shown in FIGS. 3 and 4, is connected to first arm 10 by an adjustable bracket 12 which can be adjusted in proximal-distal directions only in a slot 13 in arm 10 and locked in position by a retaining nut 14, and the femur clamp 5 can be angularly adjusted in relation to bracket 12 in a slot 15 provided on the bracket and locked in position by nut 16.

The connector 3 for connecting the support element 1 to the femoral prosthesis which is to be implanted is shown in more detail in FIG. 8 and comprises a sleeve 20 secured to second arm 11 and in which is located a securing stud 21.

The proximal end 22 of prosthesis 4 is provided with a screw threaded bore 23 in which a screw threaded portion 24 of the stud 21 can be located. The other end of the stud is held by a nut 25.

The distal end of sleeve 20 is provided with a pair of opposed projecting keys 26 which engage in keyways 27 in the form of slots provided in an enlarged end portion of bore 23.

Thus, it will be seen that prosthesis 4 can be held in position on the arm 11 and is restrained against relative rotation by the keys 26 and the keyways 27.

With boss 17 located in slot 40 in body 30 of the clamp and held by a nut 37 the position of the clamp can be adjusted in relation to the adjustment bracket 12 to alter the radial distance from femur 6.

Drill guides 2 are carried on arm 10 by a clamping plate 40 which is held in place by a screw threaded shaft 41 retained by a nut 42. Shaft 41 passes through one of a series of four openings 43 in arm 1. As will be seen, once the guides have been fixed in position there is a predetermined distance from the guides to connector 3 for connecting the support element 1 to the femoral prosthesis 4. This distance can however be adjusted by using the alternative openings 43. Drill guides 2 are set for a position with respect to the given prosthesis so that they are fixed and aligned with holes 44 in prosthesis 4.

A typical drill bit 45 is shown in place in one of drill guides 2 and its lower operative end 46 indicates how it has been drilled through femur 6 passing through the existing holes 44 in the stem 47 and through the other side of femur 6.

Second arm 11 can be arranged to be detachable from the support element 1 and is secured to arm 10 by a plug and socket connection indicated by reference numeral 90. A triangular socket 91 is provided in arm 10 into which a triangular shaped plug on arm 11 is inserted.

The plug 92 is retained in position by a locking screw 93 in the end of the arm.

In FIG. 7 the bone of soft tissue T, which has been folded back to provide the "window" and expose femur 6, is not shown.

To carry out the surgery relating to a transfemoral osteotomy the surgeon first ensures that appropriate X-rays have been taken so that he can consider the amount of bone which needs to be removed from the femur. Once having decided this the measurements are carefully taken for further use with the apparatus according to the invention.

The soft tissue is now opened using the clamped drill guide element as described above to reveal the femur and the bone is cut appropriately to provide a proximal end C, indicated by reference numeral 49 in FIG. 7. The "window" is now opened using the clamp and drill guide element as described above. The stem 47 of prosthesis 4 is now inserted in the femoral canal and the frame in the form of arms 10 and 11 is connected to it by means of the connector 3.

Nut 14 is released to allow bracket 12 to move in slot 13 and so that it can be secured to the clamp 5 by boss 17 and nut 16 through the slot 15. The release of nut 16 allows slot 15 to be placed on boss 17 at the appropriate radial distance from the femur prior to subsequent tightening. It will be appreciated that the proximal-distal movement in the slot 13 accommodates the leg length adjustment. The ante/retroversion (version angle) adjustment is now carried out by revolving the frame about the axis of prosthesis 4 and the particular angle adjustment is set by tightening nut 16. During this angular movement prosthesis 4, which is securely attached to the support frame, revolves with it as do drill guides 2.

The proximal-distal positioning of the drill guides is set according to the pre-operative planning and they are now positioned by releasing nut 42 so that they can be located in contact with the cortex of the femur and the nut suitably tightened.

The drill guides can now be used to produce the necessary holes through the bone to accept the required bolts or pins.

In the arrangement described above two drill guides are shown but only one or any other number can be utilized if required.

The apparatus can be simply removed by releasing the stud 21 in prosthesis 4, releasing nut 16 and removing the frame. Clamp 6 can be removed separately. The "window" is now closed according to any known post-operative technique.

Figure 9:
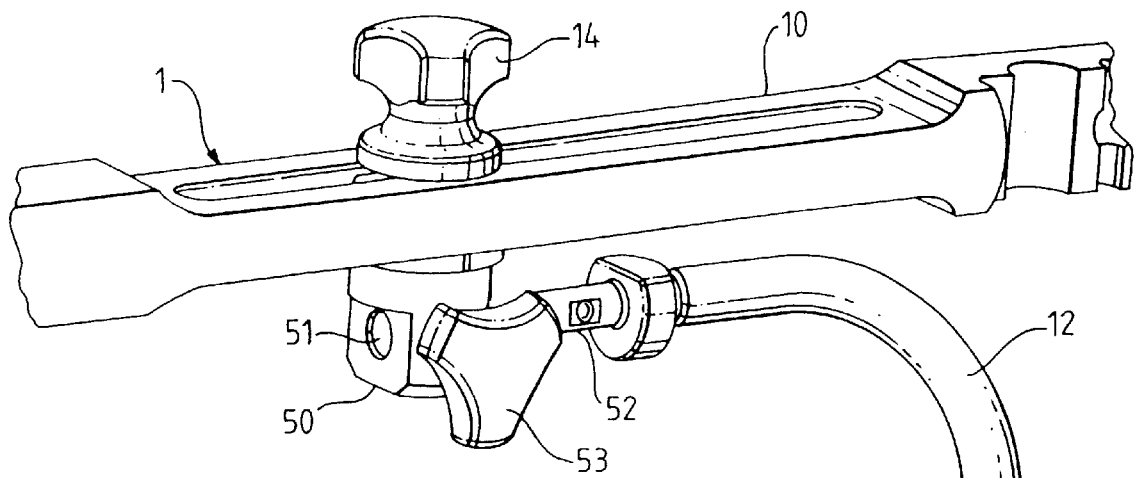
FIG. 9 is an isometric view of part of the support element.

FIG. 9 shows an alternative embodiment in which the same reference numerals are used to indicate similar parts. In this arrangement adjustable bracket 12 can be readily disconnected from first arm 10 of the L-shaped frame. In this embodiment nut 14 is shown as a hand nut and is carried on a boss 50 which has a bore 51 adapted to receive a spigot 52 provided on the end of the bracket 12. The boss 50 also carries a screw threaded locking nut 53 which can be advanced through a screw threaded bore (not shown) so that it engages against the spigot 52 where it is located in the bore 51 to clamp it in position. This embodiment enables disconnection of the assembly without having to unscrew locking nut 14 thus enabling the leg length to be set without readjustment.

Figure 10:
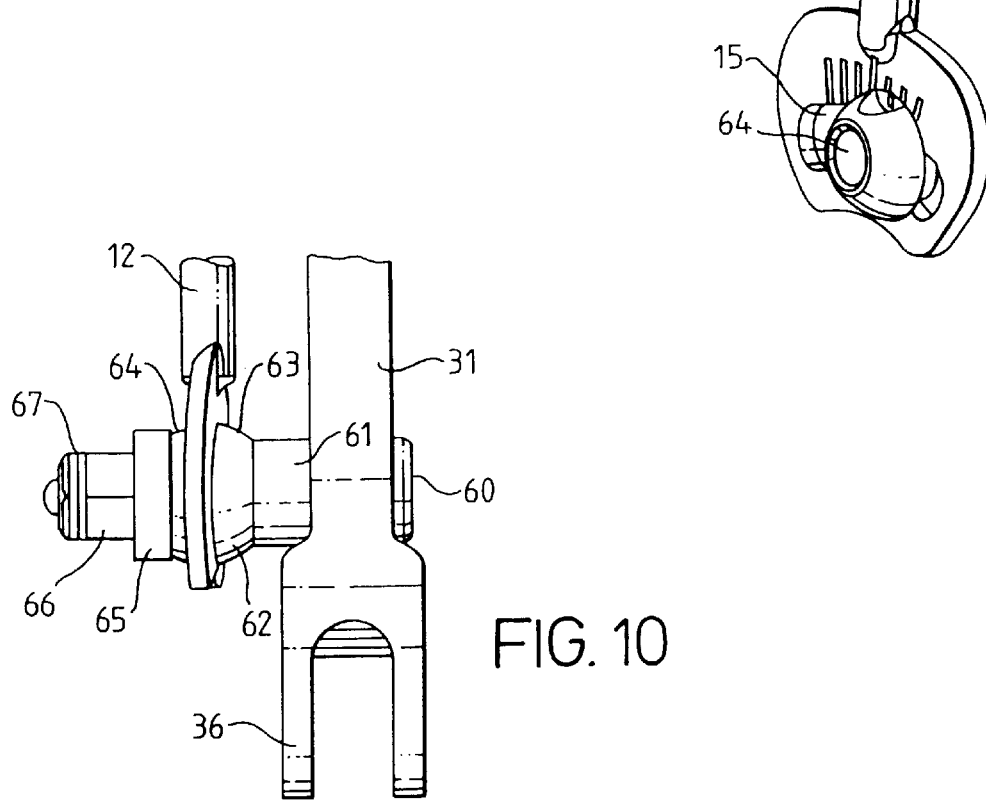
FIG. 10 is a partial side view of an alternative embodiments of the clamp device shown in FIGS. 3 and 4.
Figure 11:
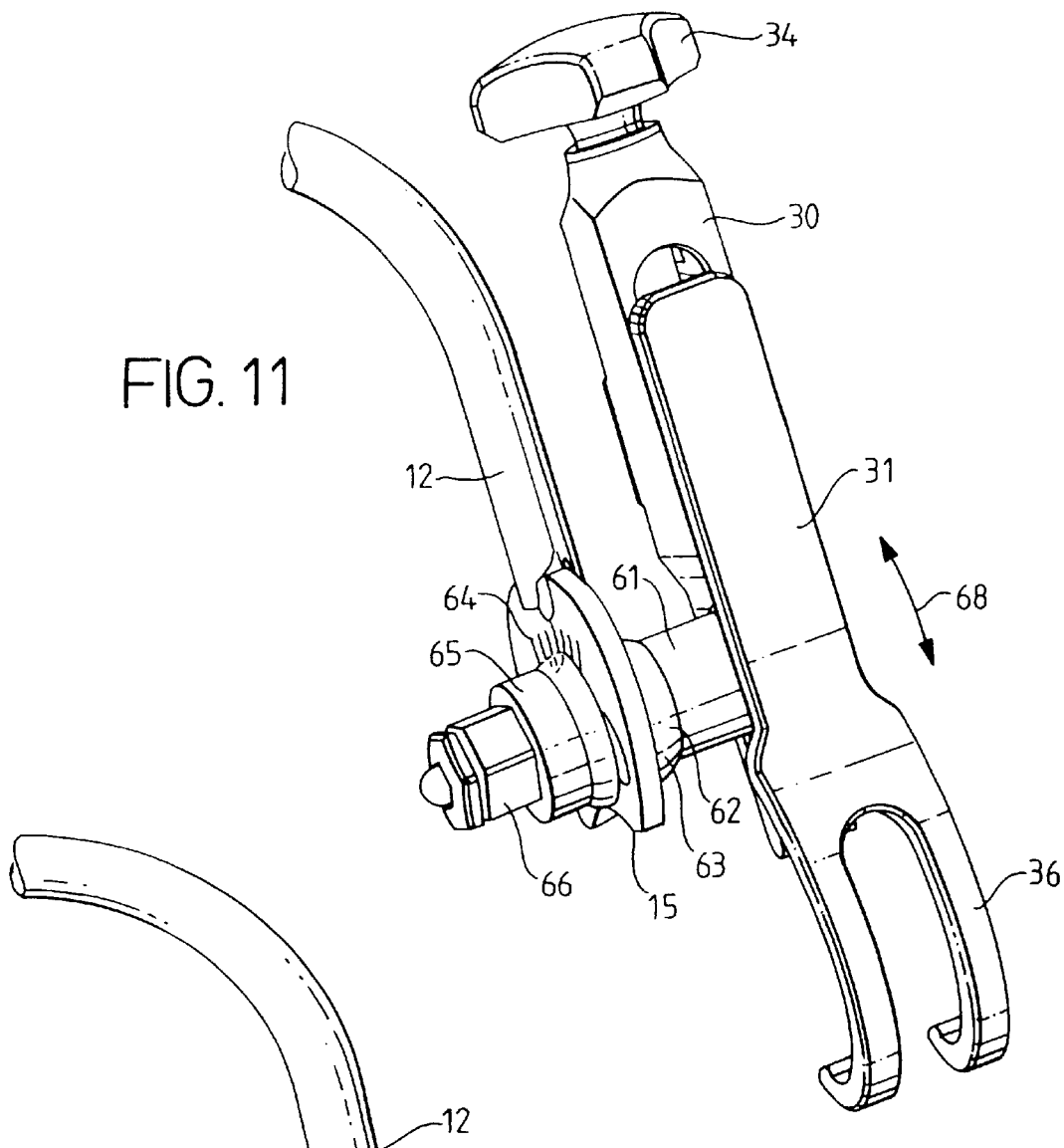
FIG. 11 is an isometric view of the embodiment shown in FIG. 10.
Figure 12:
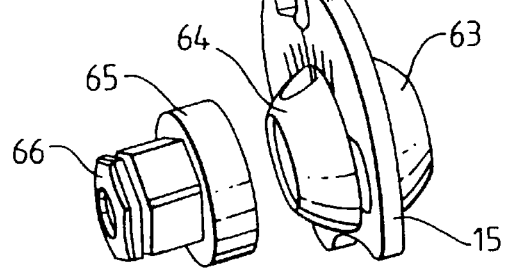
FIG. 12 is an isometric view of the embodiment shown in FIG. 9 partially dissembled.

FIGS. 10, 11 and 12 show an alternative construction for the open jawed clamp device and the same reference numerals are used to indicate similar parts to those shown in FIGS. 3 and 4. In this embodiment however, the boss 17 is replaced by a bolt 60 which extends through slot 40 and carries a spacer 61. One end 62 of the spacer 61 is dished to accommodate a part-spherically shaped washer 63. A second part spherically-shaped washer 64 is also located on the screw 60 and one side of this is housed in a dished portion 65 of a nut 66. Nut 66 has a circumferential groove 67 to accommodate resilient ring (not shown) which can act to retain a socket wrench during assembly. Each of the washers 64 and 63 also has a flat side which are located against the sides of slot 15 on bracket 12 when the whole construction is assembled together with screw 60 passing through slot 15.

With nut 66 tightened the assembly is tightly clamped together but if the nut 66 is slackened bracket 12 can align itself in three different directions by movement of the part spherical washers in the spacers 61 and 65. This enables three relative rotations, one of which is the anteversion setting and the other two rotations enable centering of the stem in the femur if the clamp is ill positioned on it.

As the attachment of the clamp to bracket 12 is also adjustable and can be clamped in position movement of the clamp in the direction of the arrows 68 on FIG. 9 this enables the automatic adoption of the femur diameter and once set can be tightly adjusted to provide rigidity of the assembly.

Figure 13:
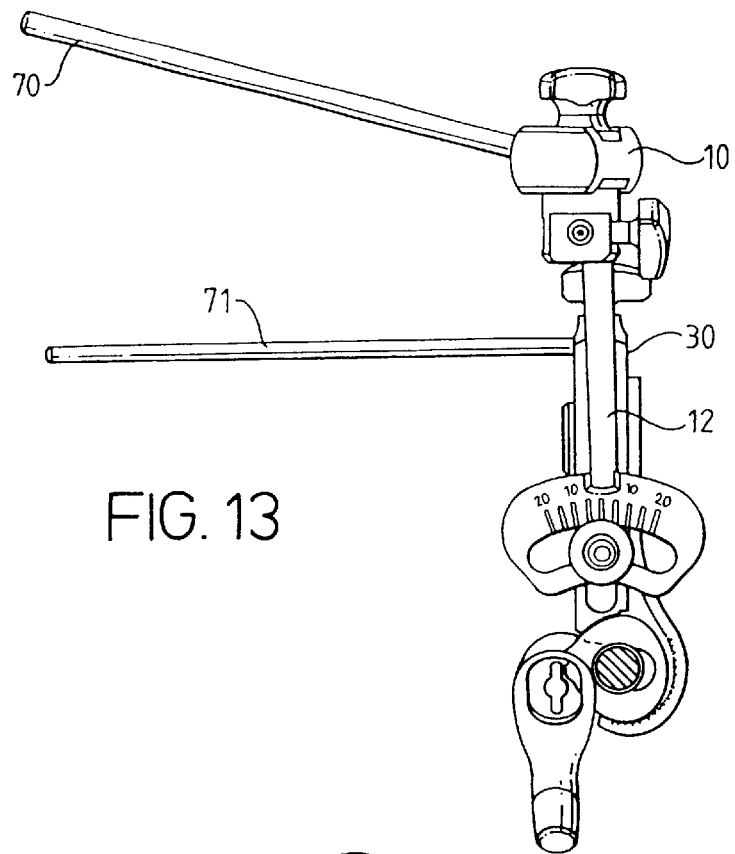
FIG. 13 is an end view of the device shown in FIG. 3 incorporating the alternative embodiments shown in FIGS. 9, 10, 11 and 12 and including visual indicator guides and with the support element in a first position.

FIG. 13 shows how visual indicator guides can be provided. Thus, a visual indicator guide arm 70 is attached to the L-shaped frame 10 in the form of a rod which extends at 15° to the axis of the first arm 10. A second indicator guide 71 which is also in the form of a rod is attached at an angle normal to the longitudinal axis of the clamp main body portion 30.

Figure 14:
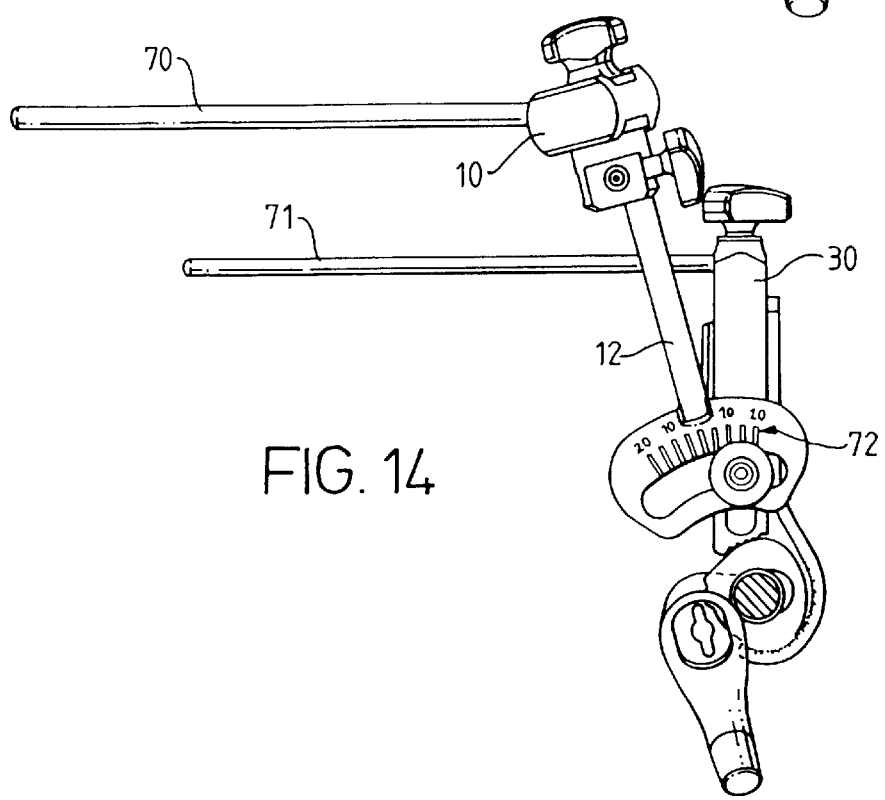
FIG. 14 is a similar view to FIG. 13 with the support element in a second aligned position.

Using the visual indicator guides the apparatus is placed in position with the clamp positioned perpendicular to the 90° knee flexion plane. This is the first position of the anteversion at 0° and this is shown in FIG. 13. In FIG. 14, the L-shaped frame 10 has been rotated until the visual indicator guides 70, 71 are parallel. In this position the frame 10 has been rotated through 15° in relation to clamp 30. Thus, the neck axis is parallel to the axis of the frame 10 and the rotation of the frame has thus created an angle between the clamp and the frame which is the anteversion angle. The exact angle of anteversion can be read from a scale indicated by reference numeral 72 provided on bracket 12.

The standard value of anteversion is 15° and this can be used as a datum when setting up the apparatus.

Figure 15:
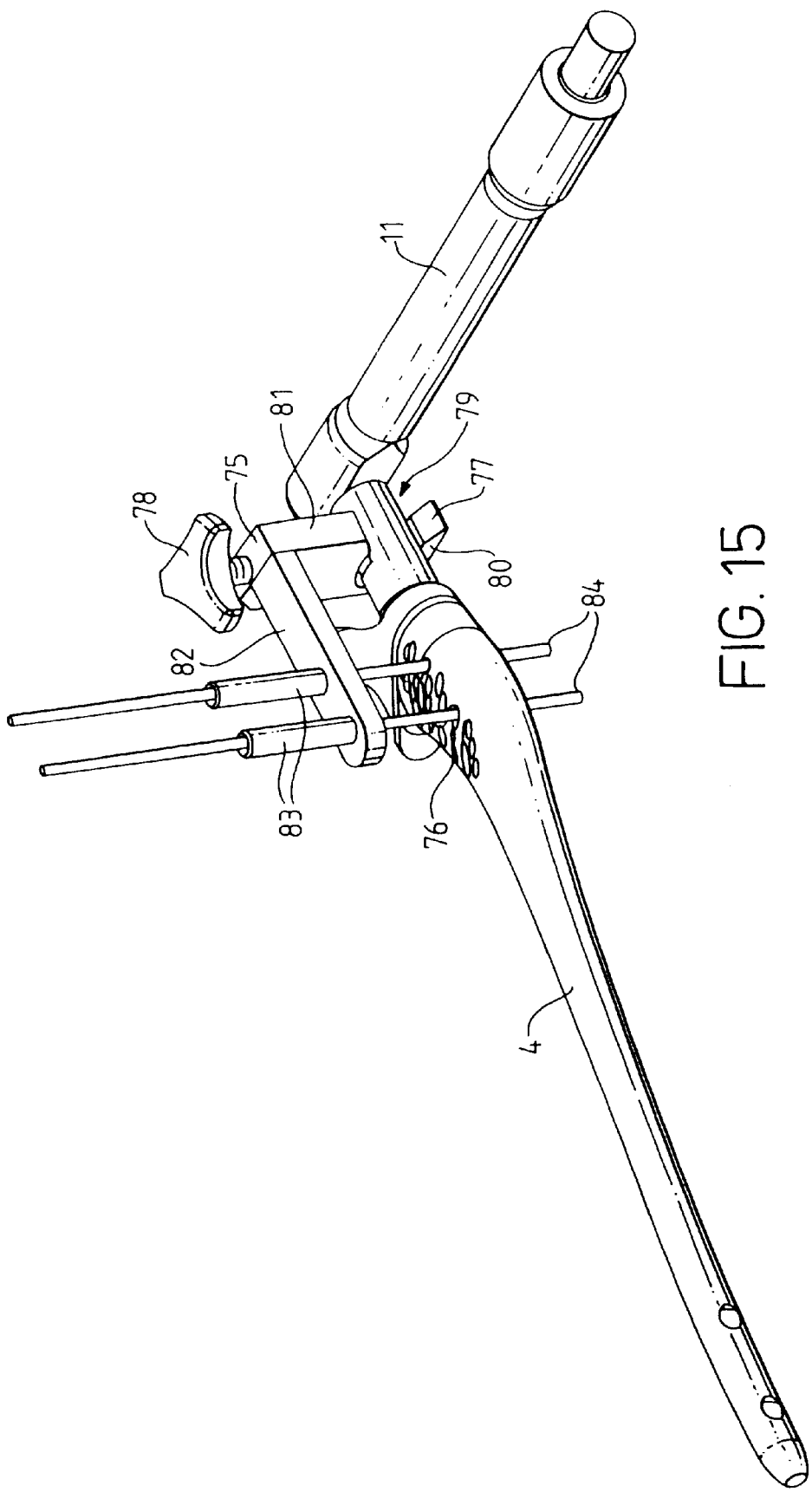
FIG. 15 is an isometric view showing a rule guide which can be clamped into position to enable holes to be made through the bone and soft tissue T when it has been folded back into position on the femur.

When the "window" is closed it is necessary to fold the soft tissue and bone which has previously been folded back to provide the window back into position and locate it around the installed prosthesis. FIG. 15 shows how a proximal drill guide 75 can be provided to guide drills through the folded back "flap" and to enable the drills to line up with pre-arranged holes 76 provided on prosthesis 4. This device is in the form of an open jawed clamping block 77 which is provided with a tightening screw 78 which passes through a threaded bore (not shown) in the block to extend into the gap 79 provided between a lower clamping jaw 80 and an upper clamping jaw 81. Clamping block 77 carries an arm 82 which supports a pair of drill guides 83.

As will be seen from FIG. 15 the prosthesis is provided with a series of openings 76. With the prosthesis in position in the support element 1, and held by second arm 11, the clamping block is placed in position and the drill guides are aligned by the use of guide rods or drills 84. With the drill guides now aligned with the openings 76 the clamping screw 78 is tightened to lock the clamping block in position. The rods or drills 84 can now be removed, the "window" is closed and the drill guides employed to guide the drill or drills to make openings in the flap of bone and soft tissue 48. The openings can then be located by passing wire hoops through the openings and suitably locating them thus ensuring that the flap of material is held in place.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A targeting apparatus for use in resectioning a femur when performing transfemoral osteotomy surgery comprising a drill guide element which includes a line of drill openings each of which is adapted to guide a drill and means for engaging an outer surface of an exposed femur for rigidly securing said drill guide element to the femur to be resectioned with the line of openings extending in a proximal/distal direction wherein the drill guide element also includes a longitudinally extending cutting guide offset from said line of openings, the guide for guiding a means for exposing the femur along a proximal/distal line.

2. The targeting apparatus as claimed in claim 1 further comprising means for altering the angular position of the drill guide element on the femur about a proximal/distal axis after it has been secured thereto.

3. The targeting apparatus as claimed in claim 1 wherein the drill guide element includes two parallel lines of drill openings.

4. The targeting apparatus as claimed in claim 1 wherein the guide is in the form of a guide slot.

5. The targeting apparatus as claimed in claim 1 wherein the drill guide element is removably connected to the securing means.

6. The targeting apparatus as claimed in claim 1 wherein which the means for securing the element to the femur is in the form of an adjustable open jawed clamp adapted to partially surround the femur with which it is to be used.

7. The targeting apparatus as claimed in claim 1 wherein the femur securing means includes means for adjusting and clamping the securing means according to the femur diameter.

8. The targeting apparatus as claimed in claim 1 wherein the means for securing the support element to the resectioned femur includes a universal joint.

9. The targeting apparatus as claimed in claim 1 further comprising a drill guide for drilling openings through the bone and soft tissue when it has been folded back into position at the proximal end of the femur.

10. A targeting apparatus for use in resectioning a femur when performing transfemoral osteotomy surgery comprising a drill guide element which includes a line of drill openings each of which is adapted to guide a drill and means for rigidly securing said drill guide element to a femur to be resectioned with the line of openings extending in a proximal/distal direction wherein the drill openings are angled in relation to each other so that the openings are more closely spaced apart on the outer side of the element than on the inner side adjacent the femur.

11. The targeting apparatus as claimed in claim 10 wherein each of the entry points of the openings on the outer side of the element serves two or more openings so that there are more entry points for openings on the inner side of the element than on the outer side.

12. A targeting apparatus for use in resectioning a femur when performing transfemoral osteotomy surgery comprising a drill guide element which includes a line of drill openings each of which is adapted to guide a drill and means for rigidly securing said drill guide element to a femur to be resectioned with the line of openings extending in a proximal/distal direction and further comprising means for locating the securing means on a partially resectioned transverse end of the femur after a first transverse cut has been made.

13. The targeting apparatus for use in performing transfemoral osteotomy surgery comprising a drill guide element which includes a line of drill openings each of which is adapted to guide a drill and means for rigidly securing said drill guide element to a femur to be resectioned with the line of openings extending in a proximal/distal direction and further comprising a support element provided with a drill guide, means for securing the support element to a resectioned femur, means for connecting the securing means for the drill guide element to the support element, and means for adjusting the angular position of the drill guide in relation to the resectioned femur about a proximal-distal axis.

14. The targeting apparatus as claimed in claim 13 wherein the support element includes means for connection to a proximal end of a femoral prosthesis.

15. The targeting apparatus as claimed in claim 13 further comprising an indicator to indicate the angular position of the drill guide relative to the resectioned femur.

16. The targeting apparatus as claimed in claim 13 further comprising means for adjusting the support element to accommodate alternative leg lengths.

17. The targeting apparatus as claimed in claim 16 further comprising means to vary the proximal-distal position of the support element in relation to the prosthesis securing means.

18. The targeting apparatus as claimed in claim 16 wherein the drill guide is located at a predetermined proximal-distal position from the means for connection to a proximal end of a femoral prosthesis.

19. The targeting apparatus as claimed in claim 13 further comprising means for locating the drill guide in alternative proximal-distal positions on the support element.

20. The targeting apparatus as claimed in claim 13 wherein two or more drill guides are provided.

21. A targeting apparatus for use in resectioning a femur when performing transfemoral osteotomy surgery comprising a drill guide element which includes a line of drill openings each of which is adapted to guide a drill and means for rigidly securing said drill guide element to a femur to be resectioned with the line of openings extending in a proximal/distal direction and further comprising a support element is in the form of an L-shaped frame, one arm of which carries the drill guide and the securing means and the other arm carrying the means for connection to a femoral prosthesis which is to be implanted.

22. The targeting apparatus as claimed in claimed 21 in which the securing means are connected to the L-shaped frame by an adjustable bracket which can be adjusted in proximal-distal directions on the frame and in relation to which the femur securing means can be angularly adjusted about a proximal-distal axis.

23. The targeting apparatus as claimed in claim 22 in which said adjustable bracket is readily removable from the L-shaped frame.

24. A targeting apparatus for use in resectioning a femur when performing transfemoral osteotomy surgery comprising a drill guide element which includes a line of drill openings each of which is adapted to guide a drill and means for rigidly securing said drill guide element to a femur to be resectioned with the line of openings extending in a proximal/distal direction and further comprising a guide for locating the resectioned proximal end of the femur.

25. The targeting apparatus as claimed in claim 24 in which said guide is carried on the femur securing means.

26. A method for resecting a long bone comprising:

attaching a drill guide onto the long bone, the drill guide having a plurality of guide holes extending parallel to a longitudinal axis of the bone;

resecting the long bone in a direction generally transverse to said longitudinal axis;

drilling a series of holes into the bone using said plurality of guide holes to form a row of perforations in the bone; and breaking the bone along said row of perforations.

27. The method as set forth in claim 26 wherein the attachment of the drill guide to the femur is accomplished by clamping the drill guide to the femur using a clamp having a tine partially surrounding the bone.

28. The method as set forth in claim 27 wherein the clamp is attached to the bone by rotating the tine around the bone.

29. The method as set forth in claim 26 further comprising the step of forming a longitudinal slit in the long bone circumferentially offset and parallel to said row of perforations.

30. The method as set forth in claim 29 further comprising the step of making said transverse bone cut between said row of perforations and said longitudinal slit.

31. A drill guide for use in resecting a long bone along a longitudinal extent of the bone comprising:

a connector for coupling the drill guide to a long bone;

a drill guide element supported by the connector, said drill guide element including a body having a plurality of drill guide openings, said openings aligned in a pair of parallel circumferentially offset rows, which rows are alignable with the longitudinal extent of the long bone to be resected.

32. The drill guide as set forth in claim 31 wherein the connector element is a clamp.

33. The drill guide as set forth in claim 32 wherein the clamp has movable tines to partially surround the bone.

34. The drill guide as claimed in claim 31 further comprising means for altering the angular position of the drill guide element on the long bone about a proximal/distal axis after it has been secured thereto.

35. The drill guide as claimed in claim 31 further comprising an indicator to indicate the angular position of the drill guide relative to the resectioned long bone.

36. A drill guide for use in resecting a long bone along a longitudinal extent of the bone comprising:

a connector for coupling the drill guide to a long bone;

a drill guide element supported by the connector, said drill guide element including a body having a plurality of drill guide openings, said openings aligned in a row, which row is alignable with the longitudinal extent of the long bone to be resected wherein the drill guide openings are angled in relation to each other so that the openings are more closely spaced apart on the outer side of the element than on the inner side adjacent the long bone.

37. The drill guide as claimed in claim 36 wherein each of the entry points of the openings on the outer side of the element serves two or more openings so that there are more entry points for openings on the inner side of the element than on the outer side.

38. A drill guide for use in resecting a long bone along a longitudinal extent of the bone comprising:

a connector for coupling the drill guide to a long bone;

a drill guide element supported by the connector, said drill guide element including a body having a plurality of drill guide openings, said openings aligned in a row, which row is alignable with the longitudinal extent of the long bone to be resected and further comprising a guide for locating the resectioned proximal end of the long bone.

39. The drill guide as claimed in claim 38 in which said guide is carried on the connector for coupling the drill guide to the long bone.

40. A drill guide for use in resecting a long bone along a longitudinal extent of the bone comprising:

a connector for coupling the drill guide to a long bone;

a drill guide element supported by the connector, said drill guide element including a body having a plurality of drill guide openings, said openings aligned in a row, which row is alignable with the longitudinal extent of the long bone to be resected and further comprising a support element in the form of an L-shaped frame, a first arm of which carries the drill guide element and the connector for coupling to the long bone and a second arm which carries a connector for connection to a prosthesis which is to be implanted.

41. The drill guide as claimed in claim 40 wherein the connector for coupling to a long bone is connected to the L-shaped frame by an adjustable bracket which can be adjusted in proximal-distal direction on the frame and in relation to which the long bone connector can be angularly adjusted about a proximal-distal axis.

42. The drill guide as claimed in claim 41 wherein said adjustable bracket is readily removable from the L-shaped frame.

* * * * *